US00PP32493P2

(12) United States Plant Patent
Bedard

(10) Patent No.: US PP32,493 P2
(45) Date of Patent: Nov. 24, 2020

(54) HYBRID TEA ROSE PLANT NAMED 'WEKYOOPEDKO'

(50) Latin Name: *Rosa hybrida*
Varietal Denomination: WEKyoopedko

(71) Applicant: Early Morning LLC, Lawrenceburg, IN (US)

(72) Inventor: Christian Bedard, Rancho Cucamonga, CA (US)

(73) Assignee: Early Morning, LLC, Lawrenceburg, IN (US)

( * ) Notice: Subject to any disclaimer, the term of this patent is extended or adjusted under 35 U.S.C. 154(b) by 0 days.

(21) Appl. No.: 16/602,719

(22) Filed: Nov. 26, 2019

(51) Int. Cl.
*A01H 5/02* (2018.01)
*A01H 6/74* (2018.01)

(52) U.S. Cl.
USPC ..... Plt./131
CPC ..... *A01H 6/749* (2018.05)

(58) Field of Classification Search
USPC ..... Plt./131
CPC ..... A01H 6/749
See application file for complete search history.

(56) References Cited

U.S. PATENT DOCUMENTS

PP15,061 P2 8/2004 Zary
PP16,572 P3 5/2006 Carruth
PP26,816 P3 6/2016 Bédard

*Primary Examiner* — Anne Marie Grunberg
(74) *Attorney, Agent, or Firm* — McKee, Voorhees & Sease, PLC

(57) ABSTRACT

A new variety of Hybrid Tea rose plant suitable for garden decoration, having flowers of red and white bicolor coloration.

1 Drawing Sheet

Classification: The present invention relates to a new *Rosa hybrida* plant.

Variety denomination: The new plant has the varietal denomination 'WEKmedatasy'.

BACKGROUND OF THE INVENTION

This invention relates to a new and distinct variety of Hybrid Tea Rose. It has as its seed parent the variety known as 'WEKblunez' (U.S. Plant Pat. No. 16,572) and as its pollen parent the variety known as 'WEKyoopedko' (U.S. Plant Pat. No. 26,816).

SUMMARY OF THE INVENTION

Among the features which distinguish the new variety from other presently available and commercial rose cultivars known to the inventor are the following combinations of characteristics: its excellent color stability throughout the life of the flowers, its abundant blooms and its globular shaped flowers. The plant has an upright bushy somewhat spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKmedatasy' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKblunez' by the following combination of characteristics: whereas 'WEKmedatasy' bears medium sized flowers (about 6.7 to about 8.7 cm. in diameter) of red and white bicolor coloration, 'WEKblunez' bears significantly larger flowers (about 10.0 to about 12.2 cm. in diameter) of orchid pink coloration. The flowers of the new variety have a slight fruity fragrance, whereas the flowers of the seed parent have a strong old rose fragrance.

The new variety may be distinguished from its pollen parent, 'WEKyoopedko' by the following combination of characteristics: whereas 'WEKmedatasy' bears very double flowers (about 44 to 69 petals) of red and white bicolor coloration, 'WEKyoopedko' bears double flowers of red with lighter reverse coloration with a white 'eyezone' with significantly lesser petalage (about 15 to 24 petals). The new variety has an upright bushy somewhat spreading growing habit (about 102 to about 145 cm. spread at the widest point), whereas the pollen parent has an upright bushy narrower growing habit (about 108 to about 122 cm. spread at the widest point).

COMPARISON WITH THE CLOSEST COMMERCIALLY AVAILABLE CULTIVAR

The new variety may be distinguished from its closest commercially available cultivar, 'JACtanre' (U.S. Plant Pat. No. 15,061) by the following combination of characteristics: whereas 'WEKmedatasy' bears medium sized (about 6.7 to about 8.7 cm. in diameter) very double flowers (about 44 to 69 petals), 'JACtanre' bears significantly larger flowers (about 10.0 to about 12.0 cm. in diameter) with lesser petalage (about 35 petals). The new variety has an upright bushy somewhat spreading growing habit (about 102 to about 145 cm. spread at the widest point), whereas the closest commercially available cultivar has an upright significantly narrower growing habit (about 100 cm. spread at the widest point).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety sometimes bears its flowers singly, sometimes in clusters of two to four per stem. Flowers may be borne in regular rounded clusters on strong medium length stems (about 36 to about 66 cm.). The cluster ranges from about 12.0 to about 15.5 cm. in diameter. Outdoors, the plant blooms abundantly and nearly continuously during the growing season. The flowers have a slight fruity to tea fragrance.

BUD

The peduncle is about 2.1 to about 7.8 cm. in length, of average to somewhat heavy caliper (about 0.2 to about 0.5 cm. in diameter), and usually erect to somewhat stiff. It is somewhat rough, with few stipitate glands. Peduncle color is between 146C and 138B often heavily suffused, especially on the side exposed to the sun, with between 187B and 187A.

Before the calyx breaks, the bud is about 1.2 to about 1.9 cm. in diameter at the widest point, about 1.3 to about 2.3 cm. in length, and pointed to somewhat ovoid in shape. The surface of the bud bears between 0 to 16 foliaceous appendages with few stipitate glands, usually with slender entire foliaceous parts extending beyond the tip of the bud about ¾ or more of its length. Sometimes the foliaceous parts are stout and much cut. Bud color is between 137C and 138A often moderately suffused, especially on the side exposed to the sun, with between 187B and 187A.

The sepals are 5 per flower, about 1.8 to about 8.2 cm. in length and about 0.6 to about 1.0 cm. in width at the widest point. The outer surface color of the sepal is between 137C and 138A often moderately suffused, especially on the side exposed to the sun, with between 187B and 187A. The outer surface of the sepal is somewhat smooth and bears between 0 to 8 foliaceous appendages with few stipitate glands. The inner surface color of the sepal is near 146C broadly bordered by near 137B. After the sepals open, the inner surface color is often heavily suffused, especially on the area exposed to the sun, with between 187A and 187B. The inner surface of the sepal is covered with fine wooly tomentum; sepal margins are entire and lined with few stipitate glands and hairs. The sepals are moderately permanent, and usually straight in shape with acute apices.

The receptacle of the flower is of somewhat short length (about 0.5 to about 0.7 cm.) and average in caliper (about 0.7 to about 1.0 cm. in diameter). The receptacle is urn-shaped in form. Its surface is smooth with moderately thick fleshy walls. The receptacle color is between 144A and 138B.

As the petals open (after the calyx breaks), the bud is about 1.8 to about 2.5 cm. in diameter at the widest point, about 1.6 to about 2.9 cm. in length, and ovoid to somewhat pointed in form. The color of the under surfaces of the newly opened petals is between 54C and 49D often heavily blushed on the outermost petals with between 53A and 60A to as dark as between 187A and 187B. At the point where the petal attaches, there is a large zone of between 149D and 145D. The color of the upper surfaces of the newly opened petals is between 60A and 53A. At the point where the petal attaches, there is a large zone of between 149D and 145D.

BLOOM

When fully open, the bloom ranges from about 6.7 to about 8.7 cm. in diameter. Petalage is very double with about 44 to 69 petals and about 5 to 15 petaloids irregularly arranged. When partially open, the bloom form is somewhat high centered to ovoid, and the petals are moderately tightly spiraled to cupped with petal edges somewhat reflexed outward. When fully open, the bloom form is more cupped to moderately globular, and the petals are somewhat loosely cupped with petal edges moderately reflexed outward.

PETALS

The substance of the petals is somewhat heavy and of moderately thin thickness, with upper surfaces moderately satiny and under surfaces slightly shiny. The petals are about 2.5 to about 6.2 cm. in length and about 1.8 to about 6.4 cm. in width at the widest point. Petal margins are entire.

The outer petals are nearly round to somewhat obovate in shape with rounded apices and sometimes slightly notched with one notch.

The inner petals are broadly obovate in shape with rounded apices and sometimes slightly notched with one to two notches.

Petaloids are about 0.9 to about 4.5 cm. in length and about 0.5 to about 3.4 cm. in width at the widest point. Petaloids are irregularly shaped somewhat obovate to oblanceolate with rounded to sometimes lacerated apices.

NEWLY OPENED FLOWER

The under surface color of the outer, intermediate and inner petals is between 65D and 155B often moderately blushed with near 64C to as dark as between 53A and 61B. At the point where the petal attaches, there is a large zone of near 4D. The upper surface color of the outer, intermediate and inner petals is between 60A and 53B sometimes moderately suffused with between 187B and 53A. At the point where the petal attaches, there is a large zone of between 10D and 8D.

The under and upper surface colors of the petaloids are similar in coloration to the upper and under surfaces of the intermediate and inner petals.

The general tonality of the newly opened flower is between 60A and 53B often moderately suffused with between 53A and 187B.

THREE-DAY-OLD FLOWER

The under surface color of the outer, intermediate and inner petals is between 69A and 155B often moderately blushed with between 61B and 60B to as dark as between 53A and 60A. At the point where the petal attaches, there is a large zone of between 155A and 155D. The upper surface color of the outer, intermediate and inner petals is between 60B and 53B often moderately suffused with between 187B and 53A. At the point where the petal attaches, there is a large zone of between 155A and 155C.

The under and upper surface colors of the petaloids are similar in coloration to the upper and under surfaces of the intermediate and inner petals.

The general tonality of the three-day-old flower is between 60B and 53B often moderately suffused with between 187B and 53A.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 90) and are arranged regularly about the pistils; a few are mixed with petaloids. The filaments are of moderately short length (about 0.4 to about 0.9 cm.) most with anthers. Filaments are between 3D and 2C in color. The anthers are somewhat small for the class and all open approximately at the same time. Anther color when immature is near 20A on the external part and near 11D on the internal part. Anther color at maturity is near 164B on the external part and near 200A on the internal part. Pollen is somewhat sparse and between 18B and 19C in color.

FEMALE REPRODUCTIVE ORGANS

Pistils vary in number (average about 105). The styles are somewhat uneven, average to long in length (about 0.4 to about 1.1 cm.), average in caliper, and loosely bunched to somewhat separated. Stigma color is between 16C and 15D. Style color is between 150D and 154D often moderately suffused with between 53A and 60A. Ovaries are usually all enclosed in the calyx. The ovaries are small in size and between 158B and 158C in color.

Hips have not been observed on this variety when grown in Pomona, Calif.

FOLIAGE

The compound leaves are usually comprised of three to seven leaflets and are borne abundantly. The five-leaflet leaves are about 9.0 to about 17.5 cm. in length and about 7.7 to about 16.8 cm. in width at the widest point, moderately crisp and heavy to somewhat leathery in texture on both sides, and glossy in finish on the upper side and semi-glossy to somewhat matte in finish on the under side. The leaves have a pinnate venation pattern. The terminal leaflets are about 4.1 to about 8.7 cm. in length and about 2.5 to about 4.7 cm. in width at the widest point, shaped ovate to somewhat oval with acute apices and rounded to somewhat acute bases. Their margins are usually simply serrate.

The upper surface color of the mature leaf is between 139A and 147A. The under surface color of the mature leaf is between 147B and 191C. The under and upper colors of the leaf veins on the mature leaf are similar in coloration to the upper and under surfaces colors of the mature leaf. The upper surface color of the young leaf is between 146B and 146A, often heavily suffused with between 187B and 187A. The under surface color of the young leaf is between 146C and 191C, often heavily suffused with between 187B and 187A. The under and upper colors of the leaf veins on the young leaf are similar in coloration to the upper and under surfaces colors of the young leaf.

The rachis is about 5.0 to about 8.6 cm. in length, about 0.1 to about 0.15 cm in width at the widest point, and very smooth. The upper side is deeply grooved with very few stipitate glands on the edges of the grooves. The under side of the rachis is smooth without hair or stipitate gland. The rachis color is near 146C on the under side and near 137B on the upper side, often moderately suffused on the young leaves with between 187B and 187A.

The stipules are about 1.1 to about 2.2 cm. in length and of medium width (about 0.5 to about 0.9 cm.) with moderately long straight points that usually turn out at an angle of more than 45 degrees and often recurve toward the stem. The under and upper surface color of the stipule is between 137C and 138A. The upper and under surfaces of the stipules are smooth in texture.

The petiole is average in caliper and very smooth. The upper side is deeply grooved with very few stipitate glands on the edges of the grooves. The under side of the petiole is smooth without hair or stipitate gland. The petiole is about 0.5 to about 1.6 cm. in length and about 0.1 to about 0.15 cm in width at the widest point. The petiole color is near 146C on the under side and near 137B on the upper side, sometimes moderately suffused on the young leaves with between 187B and 187A.

The plant displays an above average degree of resistance to powdery mildew (*Sphaerotheca pannosa*), downy mildew (*Peronospora sparsa*) and rust (*Phragmidium* sp.) as compared to other commercial varieties grown under comparable conditions in Pomona, Calif. The plant's winter hardiness and drought/heat tolerance are yet to be determined.

GROWTH

The plant has an upright bushy somewhat spreading medium height growing habit (about 102 to about 160 cm. in height and about 102 to about 145 cm. spread at the widest point), with very full branching. It displays vigorous growth and the canes are of medium sized caliper for the class (about 1.3 to about 1.8 cm. in diameter at the widest point).

The color of the major stems is between 148A and 146A. The major stems are rough in texture and they bear some large prickles that are about 1.2 to about 1.7 cm. in length. The large prickles are angled slightly downward with a medium length somewhat broad oval base; prickle color is between 165C and 165B sometimes lightly suffused with near 198B. The major stem bears very few small prickles of similar shape and coloration.

The color of the branches is between 146A and 146B sometimes moderately suffused with between 187B and 187A. The branches are rough in texture and they bear few large prickles which are of similar shape to the large prickles on the major stems. The prickles are about 0.5 to about 1.4 cm. in length. Prickle color is between 165A and 200D. The branches bear very few small prickles of similar shape and coloration.

The color of the new shoots is between 146C and 146D usually heavily suffused with between 187B and 187A. The new shoots are rough in texture and they bear few large prickles which are of similar size and shape to the large prickles on the branches; prickle color is near 152C usually heavily suffused with between 187B and 187C. The shoots bear very few small prickles of similar shape and coloration.

I claim:

1. A new and distinct Hybrid Tea rose plant of the variety substantially as described and illustrated herein.

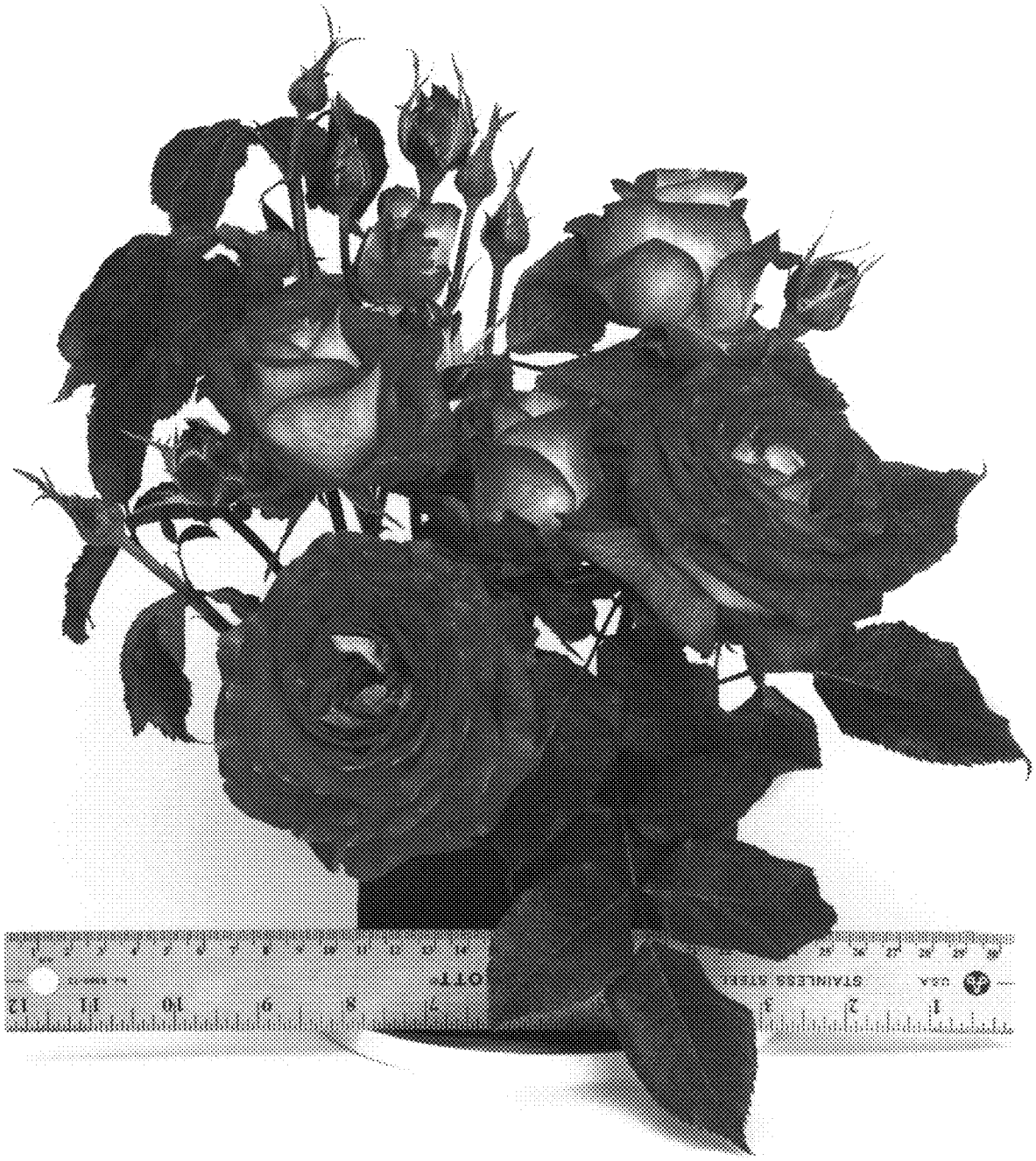

* * * * *